United States Patent
Demirev et al.

(10) Patent No.: US 7,270,948 B2
(45) Date of Patent: Sep. 18, 2007

(54) DETECTION OF MALARIA PARASITES BY MASS SPECTROMETRY

(75) Inventors: Plamen A. Demirev, Ellicott City, MD (US); Andrew B. Feldman, Columbia, MD (US); Darin Kongkasuriyachai, Walnut, CA (US); Nirbhay Kumar, Bethesda, MD (US); Peter F. Scholl, Baltimore, MD (US); David J. Sullivan, Jr., Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 383 days.

(21) Appl. No.: 10/502,834

(22) PCT Filed: Mar. 28, 2003

(86) PCT No.: PCT/US03/09642

§ 371 (c)(1),
(2), (4) Date: Jul. 28, 2004

(87) PCT Pub. No.: WO03/083130

PCT Pub. Date: Oct. 9, 2003

(65) Prior Publication Data

US 2005/0042698 A1     Feb. 24, 2005

Related U.S. Application Data

(60) Provisional application No. 60/368,234, filed on Mar. 28, 2002, provisional application No. 60/388,597, filed on Jun. 13, 2002.

(51) Int. Cl.
   *C12Q 1/00* (2006.01)
(52) U.S. Cl. .......................................................... 435/4
(58) Field of Classification Search ..................... None
   See application file for complete search history.

(56) References Cited

U.S. PATENT DOCUMENTS

| | | |
|---|---|---|
| 5,118,937 A | 6/1992 | Hillenkamp et al. |
| 5,202,561 A | 4/1993 | Giessmann et al. |
| 5,210,412 A | 5/1993 | Levis et al. |
| 5,459,063 A | 10/1995 | Cooperman et al. |
| 5,547,835 A | 8/1996 | Köster |
| 5,605,798 A | 2/1997 | Köster |
| 6,030,615 A | 2/2000 | Bucala et al. |
| 6,080,407 A | 6/2000 | Bucala et al. |
| 6,268,144 B1 | 7/2001 | Köster |
| 6,300,076 B1 | 10/2001 | Köster |
| 2002/0150903 A1 | 10/2002 | Köster |

OTHER PUBLICATIONS

Van Baar, B. L. M.; FEMS Microbiol. Rev., 2000, 24, 193-219.
Fenselau, C; Demirev, P. A.; Mass Spectrom. Rev., 2001, 20, 157-171.
Lay, J. O.; Mass Sprectrom. Rev., 2001, 20, 172-194.
Francis, S.; Sullivan, Jr., D. J.; Goldberg, D. E.; Annu. Rev. Microbiol., 1997, 51, 97-123.
Krugliak, M.; Zhang, J. M.; Ginsburg, H.; Mol. Biochem. Parasitol., 2002, 119, 249-256.
Zhang, J. M.; Krugliak, M. Ginsburg, H.; Mol. Biochem. Parasitol., 1999, 99, 129-141.
Senge, M.; Hatsher, S.; Chembiochem, 2000, 1, 247-249.
Van Vaeck, L.; Struyf, H.; Van Roy, W.; Adams, F.; Mass Spectrom. Rev., 1994, 13, 189-208.
Brown, R. S.; Wilkins, C. L.; Anal. Chem., 1986, 58, 3196-3199.
Zhan, Q.; Voumard, P.; Zenobi, R.; Anal. Chem., 1994, 66, 3259-3266.
Jones, R. M.; Lamb, J. H.; Lim, C. K.; Rapid Commun. Mass Spectrom., 1995, 9, 921-923.
Dale, M. J.; Costell, K. R.; Jones, A. C.; Langridge-Smith, P. R.; J. Mass Spectrom., 1996, 31, 590-601.
Fenyo, D.; Chait, B. T.; Johnson, T.; Lindsey, J. S.; J. Porph. Phthalocyan., 1997, 1, 93-99.
Demirev, P. A., et. al.; Anal. Chem., 2002, vol. 74, 3262-3266.
Petkewich, R.; Anal. Chem., Aug. 1, 2002, Research Profiles, 409 A.
Mann, Matthias; Nature, vol. 418, Aug. 15, 2002, 731-732.
Vigario et al.; Blood, 97(12), Jun. 15, 2001, 3966-3971.
Trager, W.; Jensen, J.B.; Science, 1976, 193, 673-675.

*Primary Examiner*—Sandra E. Saucier
(74) *Attorney, Agent, or Firm*—Francis A. Cooch

(57) ABSTRACT

Mass spectrometric techniques are provided for detecting the presence of parasites that accumulate unbound heme in red blood cells (including malaria parasites), based on the discovery that unbound heme can be detected and quantified using mass spectrometry. In one aspect of the invention, the method includes the steps of: obtaining a blood sample from the animal; preparing a test sample on a support from the blood sample, and inserting the support into a mass spectrometer for analysis. Next one obtains a mass spectrum of the test sample and determines whether the mass spectrum contains a mass/charge signature of unbound heme. If it is determined that the mass spectrum of the test sample shows the mass/charge signature of unbound heme, the animal is diagnosed as infected with malaria parasites.

24 Claims, 8 Drawing Sheets

FIG. 1
LD-TOF-MS Signals from Processed
***P. falciparum*-infected RBCs (in culture)**
and Negative Control
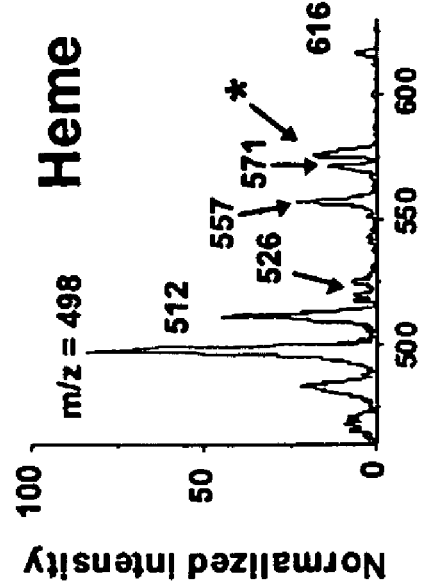
FIG. 1A — Blood - negative control — No Heme
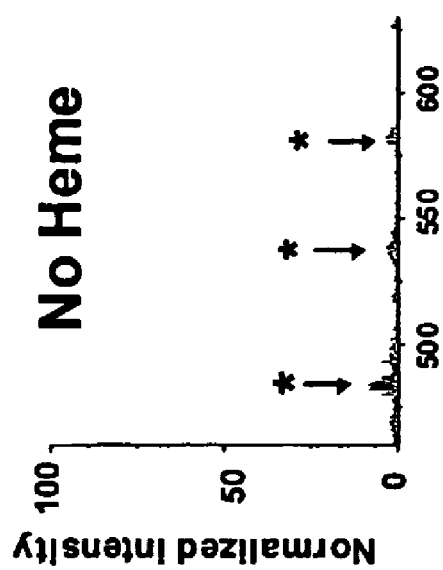
FIG. 1B — *P. falciparum* in culture — Heme

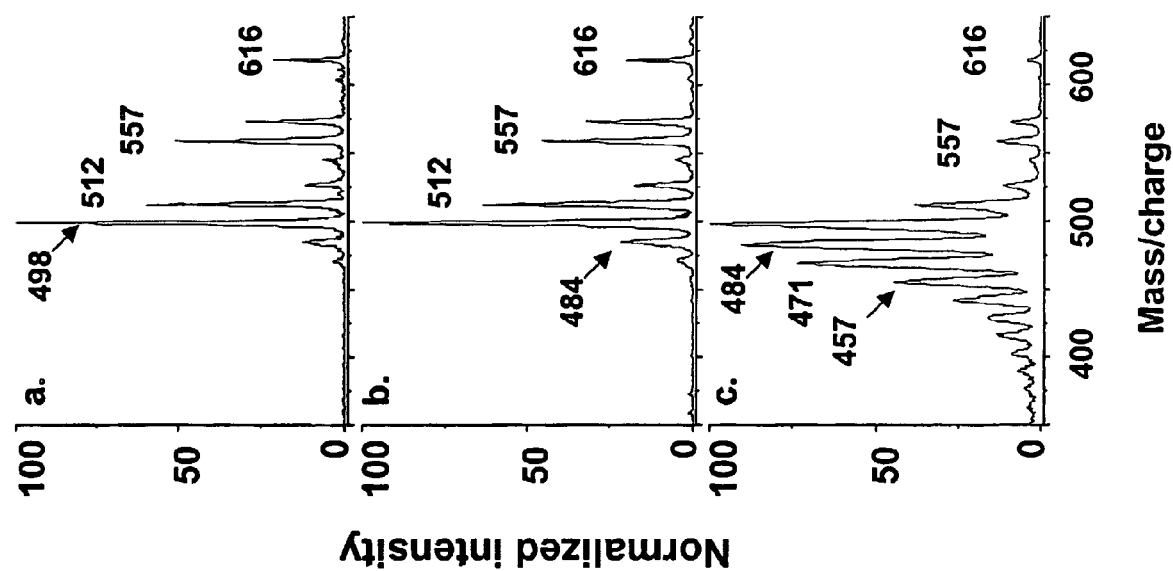
FIG. 2A, B, C

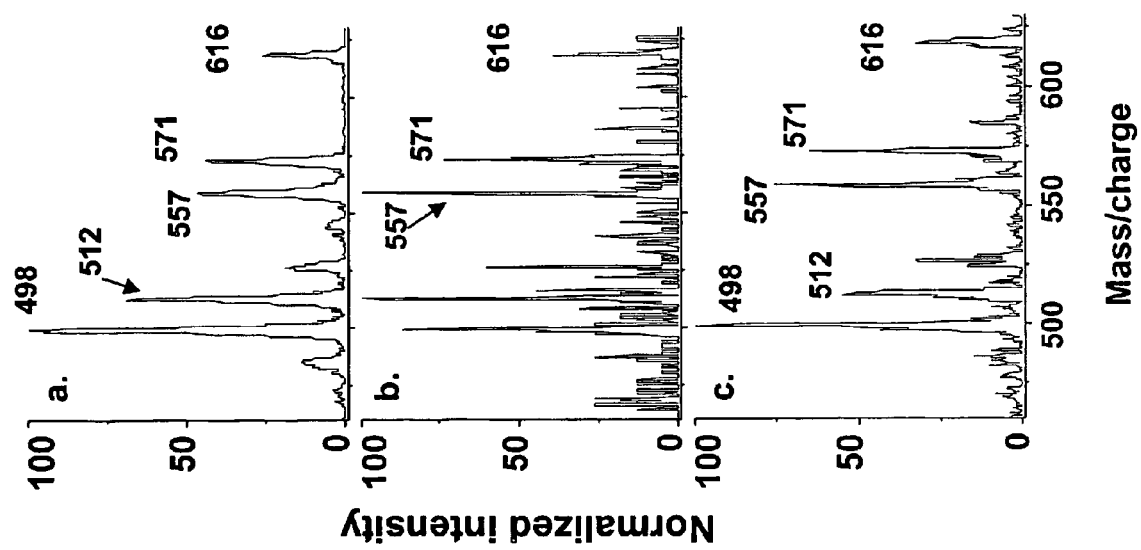
FIG. 3 A, B, C

LD-TOF MS Quantitation of Parasite Load
(*P. falciparum* in Culture)

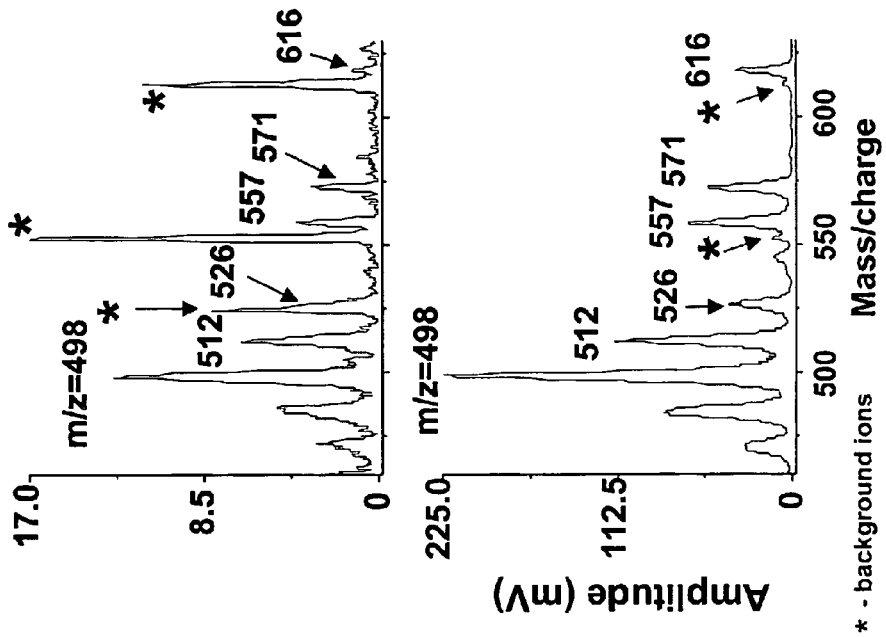
FIG. 5B 30 parasites deposited
FIG. 5C 6000 parasites deposited

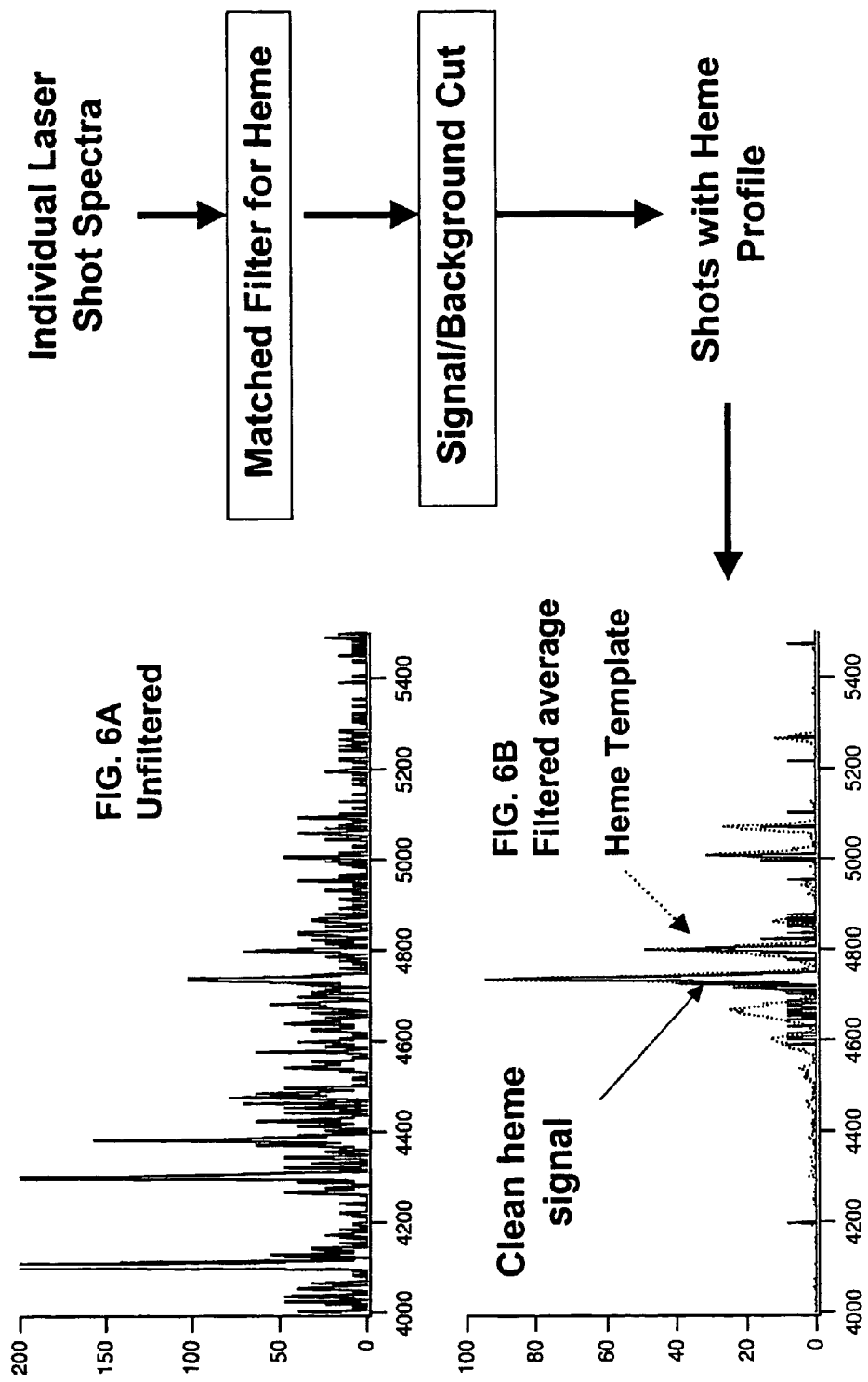

FIG. 7
Malaria Test (Human Data)
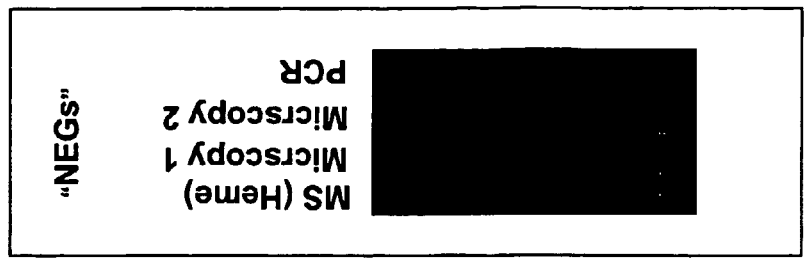
FIG. 7B
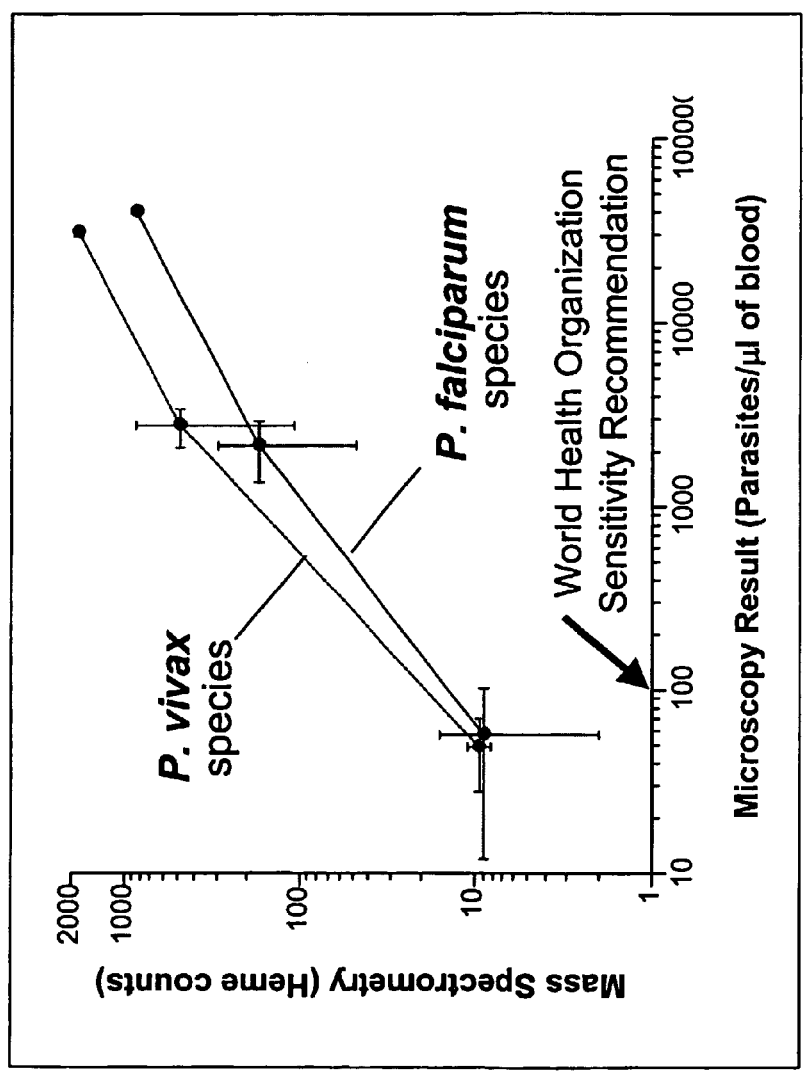
FIG. 7A

DETECTION OF MALARIA PARASITES BY MASS SPECTROMETRY

This application is a national stage filing under 35 usc §371 of international application PCT/US03/09642 and claims the benefit of prior co-pending U.S. provisional applications Nos. 60/368,234 and 60/388,597, filed on Mar. 28, 2002 and Jun. 13, 2002, respectively, the entire contents of which are hereby incorporated by reference as if fully set forth herein under 35 U.S.C. Section 119(e).

BACKGROUND OF THE INVENTION

1. Field of the Invention

The present invention relates to a method for the rapid and accurate detection and quantification of malaria-causing protozoans in the genus *Plasmodium* using mass spectrometry analysis of red blood cells. The invention is based on the discovery that unbound heme that is concentrated in malaria parasites, can be detected in a blood sample and quantified using mass spectrometry. The method can also be applied to detect and quantitate other heme-concentrating parasites including those belonging to the phylum *Apicomplexa*, and to detect any other heme-concentrating microorganism, including bacteria.

2. Description of the Related Art

Malaria is a disease affecting man and other animals, caused by different species of the parasite *Plasmodia* that are transmitted by mosquito bites. During a complex life cycle involving insect and animal hosts, the malaria parasite invades and destroys erythrocytes. Despite intense efforts to combat it, malaria still afflicts more than 500 million people. Each year, malaria infections kill between one and two million people in 103 countries, predominantly children. The emergence of drug-resistant strains and slow progress in developing an effective vaccine has compounded efforts to control the spread of the disease. Malaria in humans is caused by four different species of protozoans in the genus *Plasmodium*: *P. falciparum, P. vivax, P. malariae* and *P. ovale*, with *P. falciparum* being the most lethal.

The *Plasmodium* life cycle proceeds through several asexual and sexual stages. *Plasmodium* sporozoites, transmitted by female *Anopheles* mosquitoes, are injected into the blood of an animal host together with mosquito saliva. After initial proliferation in the liver, parasites in the merozoite stage are released back into the blood stream. A single merozoite then invades a red blood cell (RBC) and matures by forming a ring-shaped cell. In about 24 hours the matured parasite enters the trophozoite stage, during which most of the RBC cytoplasm, including hemoglobin, is catabolized. Through the final (schizont) stage in the RBC, the parasite undergoes several divisions to produce up to thirty-two new merozoites that burst the host RBC and invade new erythrocytes.

Rapid, sensitive and reliable methods for malaria detection are a factor that determines the ultimate success in controlling, restricting and eradicating this disease. Moreover, accurate parasitemia quantification is indispensable in malaria treatment, in screening new drug and candidate vaccine efficacy, and in identifying the emergence of drug-resistant parasite strains. While optical microscopy of Giemsa-stained blood smears is still considered the "gold standard" for malaria detection, it is a time consuming process requiring about one half hour per diagnosis using experienced technicians. Several new diagnostic techniques have been developed in recent years including fluorescence microscopy, PCR-based assays, serological ("dipstick") antigen detection, and flow cytometry (with or without laser light depolarization monitoring). However, currently available techniques are either too time-consuming, have low sensitivity or specificity, require trained technicians, provide poor quantitation of parasitemia, or are too expensive for mass screening. Based on the foregoing there is a clear need for a method to diagnose malaria and quantify the level of malaria parasites in an infected animal, that does not suffer the deficiencies of the prior art.

3. References

[1] Van Baar, B. L. M. *FEMS Microbiol. Rev.* 2000, 24, 193-219.

[2] Fenselau, C.; Demirev, P. A. *Mass Spectrom. Rev.* 2001, 20, 157-171.

[3] Lay, J. O. *Mass Spectrom. Rev.* 2001, 20, 172-194.

[4] Francis, S.; Sullivan, Jr., D. J.; Goldberg, D. E. *Annu. Rev. Microbiol.* 1997, 51, 97-123.

[5] Krugliak, M.; Zhang, J. M.; Ginsburg, H. *Mol. Biochem. Parasitol.* 2002, 119, 249-256.

[6] Zhang, J. M.; Krugliak, M.; Ginsburg, H. *Mol. Biochem. Parasitol.* 1999, 99, 129-141.

[7] Senge, M.; Hatsher, S. *Chembiochem* 2000, 1, 247-249.

[8] Conzemius, R. J.; Capellen, J. M. *Int. J. Mass Spectrom. Ion Phys.* 1980, 34, 197-271.

[9] Hillenkamp, F. *Int. J. Mass Spectrom. Ion Phys.* 1982, 45, 305-313.

[10] Cotter, R. J. *Anal. Chim. Acta* 1987, 195, 45-59.

[11] Vertes, A.; Gijbels, R.; Adams, F. *Laser Ionization Mass Analysis* J. Wiley, New York, 1993.

[12] Van Vaeck, L.; Struyf, H.; Van Roy, W.; Adams, F. *Mass Spectrom. Rev.* 1994, 13, 189-208.

[13] Tabet, J. C.; Jablonski, M.; Cotter, R. J.; Hunt, J. E. *Int. J. Mass Spectrom. Ion Phys.* 1985, 65, 105-117.

[14] Brown, R. S.; Wilkins, C. L. *Anal. Chem.* 1986, 58, 3196-3199.

[15] Weeding, T. L.; Steenvoorden, R. J. M.; Kistemaker. P. G.; Boon, J. J. *J. Anal. Applied Pyrol.* 1991, 20, 47-56.

[16] Zhan, Q.; Voumard, P.; Zenobi, R. *Anal. Chem.* 1994, 66, 3259-3266.

[17] Jones, R. M.; Lamb, J. H.; Lim, C. K. *Rapid Commun. Mass Spectrom.* 1995, 9, 921-923.

[18] Dale, M. J.; Costello, K. F.; Jones, A. C.; Langridge-Smith, P. R. *J. Mass Spectrom.* 1996, 31, 590-601.

[19] Fenyo, D.; Chait, B. T.; Johnson, T.; Lindsey, J. S. *J. Porph. Phthalocyan.* 1997, 1, 93-99.

[20] Demirev, P. A., et al., *Anal. Chem.* 2002, Vol. 74, 3262-3266.

[21] Petkewich, R., *Anal. Chem., Aug. 1, 2002*, Research Profiles, 409 A.

[22] Mann, Matthias, *Nature*, Vol. 418, 15 Aug. 2002, 731-732.

[23] Vigario et al., *Blood*, 97(12), Jun. 15, 2001.

[24] Koster, U.S. Patent Application Publication No. U.S. 202/0150903.

[25] Koster, U.S. Pat. No. 5,605,798.

[26] Trager, W.; Jensen, J. B. *Science* 1976, 193, 673-675.

[27] Schlichterle, M., et al., Malaria Research, $3^{rd}$ ed.; ATCC; Manassas, Va., 2000.

4. Definitions

Bound heme means a molecule that is non-covalently bound to a polypeptide chain, e.g., one heme bound to each of the four subunits of hemoglobin (the oxygen-binding hemoglobin prosthetic group).

Heme (ferriprotoporphyrin IX, $C_{34}H_{32}N_4O_4Fe$) consists of a particular planar tetrapyrrole ring system that chelates iron.

Heme-concentrating parasite means any parasite including but not limited to *Plasmodium* that concentrates unbound heme including: parasites of the phylum Plathyhelminthes (the flatworms), Order Strigeiformes, family Schistosomatidae, species Schistosoma (blood flukes causing shistosomiasis); parasites of the phylum *Apicomplexa*; and any other parasites that concentrates heme.

Malaria parasite means any species of *Plasmodium* that causes malaria.

Parasitemia means the number of parasites per unit of blood.

Unbound heme means free heme molecules, including heme molecules that are part of the malaria pigment hemozoin, e.g. heme that is not bound to each of the four subunits of hemoglobin or other protein.

SUMMARY OF THE INVENTION

Mass spectrometric techniques are provided for detecting the presence of accumulated unbound heme in blood cells (including red blood cells infected with malaria parasites), based on the discovery that unbound heme can be detected, quantified and discriminated from bound heme using mass spectrometry. In one aspect of the invention, the method includes the steps of: obtaining a blood sample from the animal; preparing a test sample on a support from the blood sample, and inserting the support into a mass spectrometer for analysis. Next one obtains a mass spectrum of the test sample and determines whether the mass spectrum shows a mass/charge signature of unbound heme. If it is determined that the mass spectrum of the test sample shows the mass/charge signature of unbound heme, the animal is diagnosed as infected with malaria parasites. In an embodiment of this aspect, the level of parasitemia of the test sample is determined by obtaining the integrated heme signal of the test sample and comparing it to one or more predetermined integrated heme signals. Each different predetermined integrated heme signal is associated with a different known level of parasitemia.

In various embodiments, the test sample can be formed in different ways. In one embodiment, referred to as the direct deposit method, the test sample is formed by diluting the blood sample in a buffer solution to form a diluted blood sample that it is deposited on a support; and dried to form the test sample. In embodiments in which it is desired to concentrate the unbound heme in the blood sample, a different technique is used. To concentrate unbound heme in a blood sample, the red blood cells are lysed to form a lysate that is then washed. The washed lysate is then resuspended in a buffered solution to form a buffered lysate, that is deposited on the support and dried to form the test sample. In some embodiments, the red blood cells (RBCs) may be lysed by sorbitol, saponin, or acetic acid.

Malaria parasites that concentrate unbound heme and that can be analyzed using the mass spectrometric methods of the present invention include *Plasmodium* protozoa including *P. vivax, P. falciparum, P. ovale* and *P. yoelli*. Other parasites or microorganisms, including bacteria, that concentrate unbound heme that can be analyzed using the mass spectrometry methods of the present invention, including: parasites of the family Schistosomatidae, species *Schistosoma* (blood flukes causing shistosomiasis); parasites of the phylum *Apicomplexa*; and any other parasites that concentrates heme.

In another aspect of the invention, the method detects the presence of microorganisms that concentrate unbound heme; where the microorganisms can be bacteria. The method includes the steps of: obtaining a sample from the environment, and preparing a test sample on a support. Preparation of the test sample may require various purification steps. This step is followed by inserting the support into a mass spectrometer, obtaining a mass spectrum of the test sample, and determining whether the mass spectrum shows a mass/charge signature of unbound heme. If it is determined that the mass spectrum of the test sample shows the mass/charge signature of unbound heme, concluding that the sample contains unbound heme-concentrating microorganisms.

The preferred mass spectrometer is a laser desorption (LD) mass spectrometer that can be equipped with a time of flight (TOF) mass analyzer. In various embodiments, mass spectrometers that differentiate based on ionization after primary ion impact (secondary ion mass spectrometry—SIMS), and those that analyze the ion mass-to-charge ratio by other means such as ion cyclotron resonance (ICR) and Fourier Transform can also be used. In various embodiments, the mass spectrometer can use either an infrared laser or a visible laser.

In one embodiment, determining whether the mass spectrum shows a mass/charge signature of unbound heme includes the step of using a matched filter for heme to reject non-specific background clutter in the mass spectrum.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 1A and B are graphs that illustrate the LD-TOF mass spectrometry signals from lysed *P. falciparum*-infected human RBCs in culture compared to uninfected controls.

FIGS. 2A, B and C are graphs that illustrate the effect of laser fluence, F, on heme mass spectra from ring-stage culture of *P. falciparum*-infected human RBCs.

FIG. 3 is a graph that illustrates the dependence of the heme ion signal on laser exposure in non-synchronized *P. falciparum* culture.

FIG. 6. is a graph that illustrates results of a match-filter-based signal processing method for extracting the heme signatures from an LD-TOF mass spectra.

FIG. 7A is a graph that shows results from LD-TOF mass spectrometry for human clinical blood samples for low, medium and high levels of *P. vivax* or *P. falciparum* malaria compared with optical microscopy analysis.

FIG. 7B is a graph of data comparing, LD-TOF MS, optical microscopy and PCR (polymerase chain reaction). The figure illustrates detection of parasite DNA (by PCR) and heme (by LD-TOF MS) on samples deemed "negative" for parasites by optical microscopy.

DETAILED DESCRIPTION

Figure 4A:
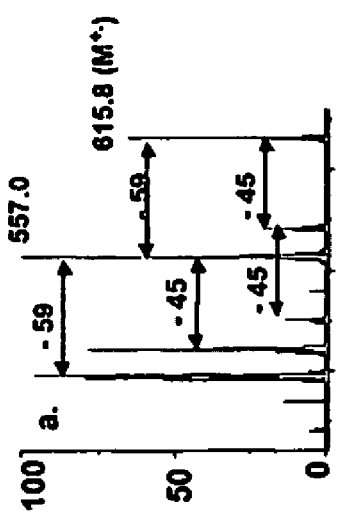
FIGS. 4A, B and C are graphs that illustrate LD mass spectra of a purified *P. falciparum*-containing sample in positive ion mode, and commercial ferriprotophyrine IX chloride samples in positive and negative ion modes.

Mass spectrometry has been developed in recent years into a viable technique for intact microorganism characterization [1-3]. Laser desorption (LD) time-of-flight (TOF) mass spectrometry, in particular, has enhanced the prospects for field-deployable, robust, automated, and miniaturized detection systems for applications in a variety of areas from microbiology to bioterrorism counter-measures. The present invention is directed to a very sensitive method for diagnosing malaria based on the discovery that mass spectrometry detects unbound heme that is concentrated in large amounts by malaria parasites inside infected RBCs and that is not detectable in normal, uninfected red blood cells. It is also directed to a very sensitive method for quantifying parasitemia. Analysis of unbound heme in blood samples using mass spectrometry according to the present invention thus provides an automated assay for malaria detection and malaria parasite quantitation that is rapid, high-throughput, accurate, quantitative, highly sensitive and inexpensive.

In the following description, for the purposes of explanation, numerous specific details are set forth in order to provide a thorough understanding of the present invention. It will be apparent, however, to one skilled in the art that the present invention may be practiced without these specific details.

1. Unbound Heme

Hemoglobin comprises 95% of RBC cytosolic protein [4] and it serves as the major source of nutrients for immature intra-erythrocytic trophozoites, providing amino acids needed for the de novo malarial protein synthesis [4,5]. Heme (FP, ferriprotoporphyrin IX)—the oxygen-binding hemoglobin prosthetic group—is liberated during hemoglobin proteolysis. Intraparasitic unbound heme concentration reaches almost 0.4 molar during some stages of intraerythrocytic *Plasmodium* growth. Unbound heme is sequestered in the form of insoluble, microscopically observable hemozoin crystals (malaria pigment) in *Plasmodium* food vacuoles [4]. It was the observation in 1897 by Ronald Ross of pigment granules in the digestive tract of *Anopheles* mosquitoes that was the crucial step in establishing the missing links between parasite proliferation, spreading and transmission of malaria. Hemozoin formation alleviates the considerable oxidative stress from the extremely toxic intra-parasitic concentration of free heme, that otherwise would kill the parasite. This detoxification mechanism is a unique evolutionary feature of *Plasmodium* (and other *Apicomplexans*), and many effective anti-malarial drugs target the disruption of hemozoin formation [6,7]. Heme and other porphyrins, such as zinc protoporphyrin IX, are abundant in normal blood samples. However, they do not exist in a free state, but are bound or chelated by a variety of biomolecules such as hemoglobin, hemopexin and albumin. This complexed or bound heme is typically compartmentalized within specialized cells such as erythrocytes and hepatocytes.

Laser desorption mass spectrometry is known to be particularly well suited for the analysis of porphyrins such as unbound heme [8-12]. Both infrared (IR) and ultraviolet (UV) laser desorption mass spectrometry have been applied for structural characterization of natural porphyrins and their metabolites, synthetic monomeric porphyrins (e.g., used in photodynamic therapy), porphyrin polymers and multimeric arrays [13-19]. The protoporphyrin molecule, which can have different side chain molecule groups, contains 22 pi-electron conjugated system and is an efficient photo-absorber in the visible and near ultraviolet range. This feature combined with their low ionization potential, warrants that mass spectrometry will possess extremely low detection limits for porphyrins.

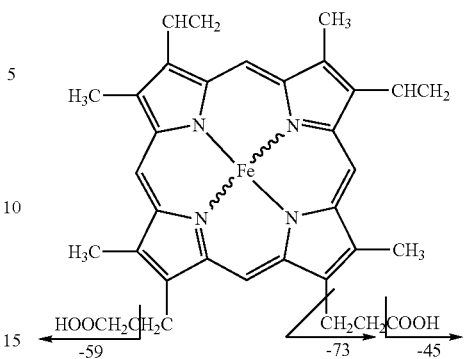

Under normal physiologic conditions, the binding or complexing of heme and other porphyrins to various intracellular proteins prevents their direct detection by LD mass spectrometric analysis. Bound heme is mass spectrometrically "silent" by LD-TOF mass spectrometry. It has now been discovered that the unbound heme, which is hyperconcentrated inside malaria parasites that have infected host RBCs, is a biomarker of malaria infection that is detectable and quantifiable by LD mass spectrometry, especially using a TOF mass analyzer. [ref. 20, the entire contents of which is hereby incorporated by reference as if fully set forth herein; and U.S. Provisional Application Nos. 60/368,234 and 60/388,597. ] Methods are described herein for diagnosing malaria by detecting the presence of unbound heme in a blood sample indicating the presence of malaria parasites. Methods for quantifying parasitemia using the mass spectrometric methods of the present invention are able to detect levels of parasitemia as low as 10 *P. falciparum* parasites/microliter blood. The methodology can be applied to other fields where detection of unbound heme is of diagnostic value. For example, the detection of occult blood in bodily fluids could be performed using LD-TOF mass spectrometry analysis. In such cases, detection would be preceded by appropriate sample treatments to release the bound heme.

2. Mass Spectrometry

Mass spectrometry has been developed in recent years into a viable technique for intact microorganism characterization [7-9]. Laser desorption ionization (LD) time-of-flight (TOF) mass spectrometry, in particular, has enhanced the prospects for field-deployable, robust, automated, and miniaturized detection systems for applications in a variety of areas—from microbiology to bioterrorism counter-measures. The ultraviolet or visible light LD-TOF mass spectrometer is preferred for use in the present invention.

In general, mass spectrometry provides a means of "weighing" individual molecules by ionizing the molecules in a vacuum. Under the influence of combinations of electric and magnetic fields, the ions follow trajectories depending on their individual mass (m) and charge (z). In the range of molecules with low molecular weight, mass spectrometry has long been part of the routine physical-organic repertoire for analysis and characterization of organic molecules by the determination of the mass of the parent molecular ion. In addition, by virtue of its excess internal energy, the molecular ion is fragmented, forming secondary ions. Such fragmentation pattern pathways very often allow the derivation of detailed structural information. Many applications of mass spectrometric methods are known in the art, particularly in the field of bioscience, and can be found summarized in Methods of Enzymology, Vol. 193:"Mass Spectrometry" (J. A. McCloskey, editor), 1990, Academic Press, New York.

Mass spectrometry has been used to detect particular nucleic acid molecules and sequences from infectious microorganisms [24, 25]; however, the use of mass spectrometry to detect microorganisms in a biological sample from the presence/absence of unbound accumulated heme has not been reported.

All of the experiments described herein use the LD-TOF mass spectrometery without a matrix to detect the presence of unbound heme in blood samples. The unbound heme hyperconcentrated in malaria parasites that have invaded host RBCs acts like a matrix to provide quantitative measurements that enable the estimation of the number of parasites in a sample.

Although the LD-TOF mass spectrometer was used in the experiments described herein, other mass spectrometers can also be used. For example, mass spectrometers that differentiate based on ionization after primary ion impact (secondary ion mass spectrometry —SIMS), and those that analyze the ion mass-to-charge ratio by other means such as ion cyclotron resonance (ICR) and Fourier Transform. For SIMS, the samples are typically bombarded by atomic or polyatomic ions with energies from thousands of electron volts (keV) to millions of electron volts (MeV); secondary ions such as heme molecular ions and heme fragments are desorbed/sputtered and then mass analyzed by, e.g., a TOF or a double-focusing mass analyzer. Even more detailed information on the specific structure of the analyzed molecule can be obtained using a mass spectrometry/mass spectrometry (tandem) system, e.g., quadrupole-TOF configuration. This will be useful for malaria detection under conditions of very high background in the m/z (mass-to-charge ratio) range where heme biomarker ions are detected.

Matrix assisted laser desorption ionization (MALDI) mass spectrometry does not work for analyzing unbound heme in blood samples if a low mass organic acid (a matrix) is used, because the acid matrix causes release of heme from hemoglobin. Alternatively, a non-acidic liquid matrix containing, e.g., suspended copper or platinum nanoparticles may enable MALDI to work for detecting unbound heme.

Various mass analyzers can be used for LD mass spectrometry, e.g., magnetic sector/magnetic deflection instruments, single or triple quadrupole mode (mass spectrometry/ mass spectrometry), Fourier transform and time-of-flight (TOF) configurations that are known in the art of mass spectrometry. In the experiments that follow, frozen sample solutions were thawed, and 0.3 microliters from each sample was deposited in a 2×1 mm² well on a stainless steel sample holder for LD-TOF mass spectrometry analysis. Samples were allowed to dry in air prior to introduction into the instrument. Commercial samples of protoporphyrin IX (PP, composition $C_{34}H_{34}N_4O_4$, $M_{mono}$=562.257, $M_{ave}$=562.667 Da) and ferriprotoporphyrin IX ($C_{34}H_{32}N_4O_4Fe$, $M_{mono}$=616.176, $M_{ave}$=616.487 Da) were obtained from Sigma Chemical Co. (St Louis, Mo.) and used without further purification. These compounds were dissolved in chloroform and 0.3 microliters were deposited on the stainless steel slide, again without a matrix, prior to LD-TOF mass spectrometry. External calibration in both polarities was performed with CsI cluster ions.

Positive and negative ion mass spectra were obtained on a Kompact MALDI 4 (Kratos Analytical Instruments, Chestnut Ridge, N.Y.) time-of-flight instrument at (+/−) 20 kV nominal accelerating voltage. An $N_2$ laser ("VSL-337ND" Laser Science Inc., MA, provided with the instrument) had an estimated fluence of 10 mJ/cm² (mJ per square centimeter) before attenuation (0.2 mJ average energy/pulse at 337 nm (nanometer) laser wavelength, pulse duration 4 ns). Pulsed ion (delayed) extraction was optimized for ion focusing and transmission at m/z 1200. Spectra were acquired in linear and reflectron modes. Unless otherwise stated, each spectrum was the average of 100 consecutive laser shot traces, with the beam incrementally moved "rastered linearly" after each laser shot across the entire sample well. A beam density of p130 (instrument setting) was optimal for detecting hyper-concentrated heme in parasites. At this beam density, no heme was detected in control blood samples, while *P. falciparum*-infected human RBCs showed a strong signal and a unique, reproducible mass/charge signature for heme. FIG. 1. FIGS. 1A and B are graphs that illustrate the LD-TOF mass spectrometry signals from lysed *P. falciparum*-infected human RBCs in culture compared to uninfected controls. Blood samples in FIG. 1 were lysed and concentrated as described in Example 1 before mass spectrometry analysis.

The LD-TOF mass spectral signature of heme is characterized by peaks at mass/charge values of 498, 512, 526, 557, 571 and 616, as shown in FIG. 1B.

The effects of laser fluence F (laser pulse energy per unit area) and laser exposure (repetitive laser irradiation) on signal duration from the same sample were tested. The existence of a laser fluence threshold ($F_{th}$) for detection of PP and FP was observed. The absolute value of $F_{th}$ is a function of the amount of parasite sample deposited—lower amounts are detected at higher $F_{th}$. Above threshold, the ion signal increases faster than linear as a function of fluence. This is an indication that laser desorption/ionization results from multiphoton absorption processes. To break up the RBCs, the blood samples in FIGS. 1-5 were lysed and washed as is described in Example 1 to concentrate the free, unbound heme in the sample for mass spectrometric analysis. FIG. 2 shows the effect of laser fluence F on heme mass spectra from ring-stage culture of *P. falciparum*-infected human RBCs prepared as described in Example 1. FIG. 2A has an initial F=100 mJ/cm²; in 2B F=160 mJ/cm² (1.6× higher); and in 2C F=290 mJ/cm² (2.9× higher). Blood samples in FIG. 2 were lysed and concentrated as described in Example 1 before mass spectrometry analysis.

The degree of fragmentation of the heme molecule also increases with laser fluence from 100 to 290 mJ/cm². Increased abundance of non-specific fragment ions, such as vinyl or methyl group losses, below m/z 498 was observed at a fluence of 290. (FIG. 2C).

FIG. 3 is a graph that illustrates the dependence of the heme ion signal on laser exposure in non-synchronized *P. falciparum* culture prepared as described in Example 1. FIG. 3A shows a mass spectrum (normalized to 30 mV detector response) from averaging of 100 laser shots at fluence F=100 mJ/cm². FIG. 3B shows mass spectrum (normalized to 1.2 mV) obtained from averaging of 100 laser shots at F=100 ml/cm² after 600 laser shots at F=100 mJ/cm², rastered across the sample. FIG. 3C shows spectrum (normalized to 7 mV) obtained by averaging of 100 laser shots at F=130 mJ/cm², after exposure to 700 laser shots rastered across the same sample at F=100 mJ/cm². Blood samples in FIG. 3 were lysed and concentrated as described in Example 1 before mass spectrometry analysis.

While the signal from a sample decreases with increased laser exposure, the presence of parasites can be confirmed even after several hundred consecutive laser shots (FIG. 3A). The nature of the phenomenon of signal decrease as a function of exposure is not clear, since the sample is not ablated (as revealed by optical examination). Signal decrease is probably related to photochemical processes occurring in the sample and changing its properties. Furthermore, increasing the fluence by a factor of 1.3 generates an appreciable signal even after 700 laser shots at lower fluence levels (FIG. 3C). Both laser fluence and laser exposure effects indicate that the threshold for parasite detection can be lowered further by accumulating and averaging spectra from a higher number of laser shots and at varying fluence levels. On the other hand, these instrumental factors have to be taken into account when the LD method is applied for parasitemia quantification. The results show that LD mass spectrometry is capable of detecting and unambiguously identifying heme-concentrating *Plasmodium* species in purified blood samples on the order of 10 parasites/microliter of blood. The LD-TOF mass spectrometric analysis of *Plasmodium* can be multiplexed and used for rapid high-throughput screening on large batches of dried blood samples.

To get the best analysis of a blood sample using mass spectrometry, the sample should be spread as thinly as possible so that the RBCs do not stack on top of one another or clump together. Using the direct deposit method of sample analysis described in detail below, blood samples with a normal hematocrit of about 50% were diluted ten-fold with phosphate buffered saline to a hematocrit of about 5% before being dropped onto the slide and allowed to dry. The dilution of the sample needs to be adjusted based on the hematocrit. If the sample has a low hematocrit due to anemia, for example, it should not be diluted as much as a sample with a normal hematocrit otherwise the number of heme detections may drop below statistically significant levels as is discussed in more detail below. Other solvents can also be used, such as water and other buffered solutions. Solvents that may hydrolyze or lyse the red blood cell can also be used as long as the solvents do not release the bound heme. Any method known in the art to produce a thin layer of sample can be used. Further, any material compatible with the mass spectrometer can be used to introduce the sample into the mass spectrometer for analysis, including glass, paper and plastic.

2. Purified *P. falciparum*-Containing Cultured Human RBCs Show Strong, Signal Specific Heme Signatures Using LD Mass Spectrometry In order to analyze the unbound heme sequestered in the malaria parasite as hemozoin by mass spectrometry, the parasite should be broken open to permit volitilization of the unbound heme. To break up the RBCs, the blood samples in FIGS. 1-5 were lysed and washed as is described in Example 1 to concentrate the free, unbound heme in the sample for mass spectrometric analysis. It was later discovered that these preparatory steps are not required to detect unbound heme in parasites in the samples. Both the RBCs and the parasites inside infected cells are opened up once the sample is inserted into the mass spectrometer, possibly by the vacuum inside the machine, thus permitting volatilization of the unbound heme concentrated inside the parasites. This unexpected discovery means that unbound heme can be assayed in unprocessed, dried blood samples (referred to as the direct deposit method), which simplifies the procedure and is described in Example 2, FIG. 6. However, the lysis/concentration method is advantageous where low levels of parasite detection is desired, for example in patients with low parasitemia levels for early detection or in patients who are anemic.

FIG. 1A and FIG. 1B show the results of experiments conducted on lysed RBCs that were frozen and thawed before LD-TOF mass spectrometry analysis. Mass spectra from a purified non-synchronized *P. falciparum* culture and a negative control (purified blood sample not infected with *P. falciparum*) are compared. The negative control of non-infected blood analyzed by LD-TOF shows no heme (FIG. 1A) using a laser intensity of p140; almost no ions are observed in the range from m/z 400 to 650 from the control. By contrast, cultured blood cells infected with *P. falciparum* show a distinct, reproducible heme signature with heme-specific mass/charge peaks at 498, 512, 526, 557, 571, and 616. (FIG. 1B).

Figure 4B:
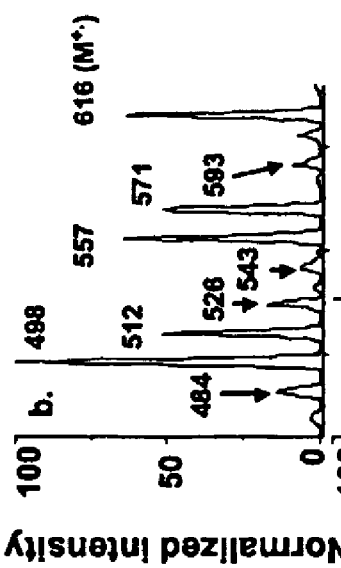
Figure 4C:
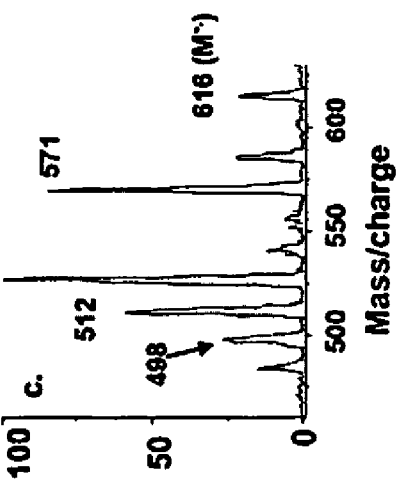

Direct LD-TOF mass spectra of purified *P. falciparum*-containing RBCs and commercial ferriprotoporphyrin IX (FP) samples are presented in FIGS. 4A, B and C. LD-TOF mass spectra of a lysed *P. falciparum*-containing sample (positive ions and reflectron mode with intensity normalized to 1.5 mV detector response value) is shown in FIG. 4A. The LD-TOF mass spectrum of a commercial ferriprotoporphyrin IX chloride sample is shown in FIG. 4B (positive ions and linear mode with intensity normalized to 289 mV). FIG. 4C shows the LD-TOF mass spectrum of commercial ferriprotoporphyrin IX chloride run this time with negative ions in linear mode and intensity normalized to 21 mV. In both positive and negative ion modes, intense molecular ion peaks are observed, with masses corresponding to the heme radical ion species $M^+$ or $M^-$, respectively (experimental M=616 Da).

No doubly- or triply-charged ions are detected in either positive or negative ionization mode. Under otherwise identical LD-TOF instrumental conditions, the signal intensity in the positive ion mode is about an order of magnitude higher, compared to negative ions, for both PP and FP. While the mass resolution at m/z 600 in reflectron mode is a factor of 4 higher (1200 full width at half maximum—FWHM), compared to linear mode (300 FWHM), the signal in linear mode is a factor of 10 to 100 more intense. In order to achieve lower detection limits, positive ion linear mode spectra were acquired from parasite-containing samples. Characteristic (heme "signature") fragment ions at m/z 498, 512, 526, 557, 571, and 616 were observed. Their masses correspond to consecutive losses of 45 atomic mass units (COOH), 59 atomic mass units ($CH_2COOH$) or 73 atomic mass units ($CH_2CH_2COOH$) from $M^+$ or $M^-$, respectively, and are directly correlated with the heme structure depicted above.

3. Quantification of Parasitemia Levels Using LD-TOF

Figure 5:
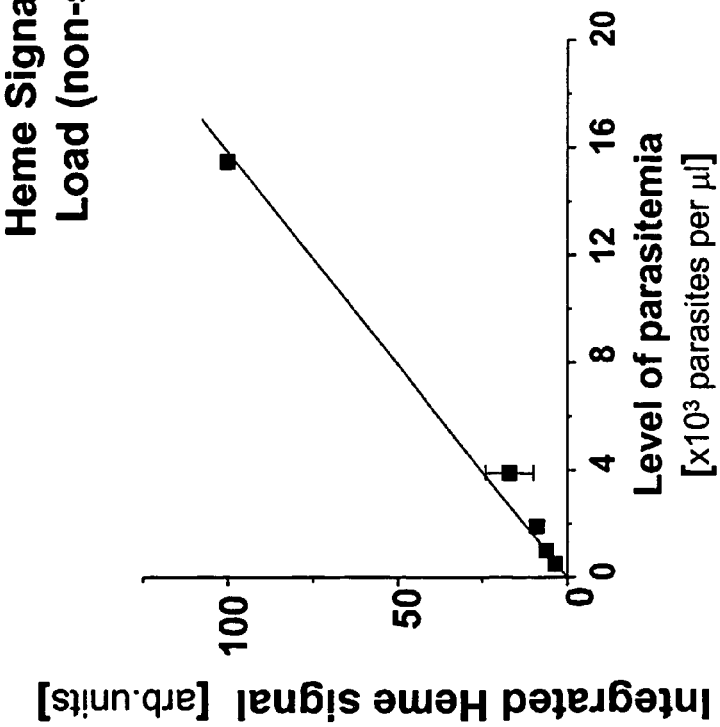
FIGS. 5A, B and C are positive ion LD mass spectra from purified ring-stage cultures that were lysed and washed.

The spectral signal variation as a function of sample parasitemia level is presented in FIG. 5. FIGS. 5A, B and C are positive ion LD mass spectra from lysed and washed samples of ring-stage cultures prepared as described in Example 1. FIG. 5A is a graph of 30 ring-stage parasites deposited (intensity normalized to 17 mV detector response value); and FIG. 5B is a graph of 6000 parasites deposited (intensity normalized to 225 mV detector response value). Peaks, marked with an asterisk, originate from contaminants unrelated to the heme. There is a linear correlation between signal intensity and the amount of parasite material deposited for samples containing known amounts of from about 500 to about $1.55 \times 10^4$ of non-synchronized *P. falciparum* parasites per microliter (as determined by optical microscopy). FIG. 5A. By non-synchronized it is meant parasites in various stages of development.

The suitability of the method for in vivo detection of *P. falciparum* infection in patients was examined using a synchronized culture with predominantly ring-stage parasites. In contrast to the other three human malaria species infections, erythrocytes containing *P. falciparum* in later developmental (trophozoite and schizont) stages adhere to endothelial cells on the inside of the blood vessels. In effect, *P. falciparum*-infected RBCs are taken out of the blood, and only RBCs with immature (ring-stage) parasites circulate freely. The ring-stage culture examined had an initial parasitemia level of $2 \times 10^4$ parasites per microliter. A series of three-fold dilutions gave a sample containing a known amount of 80 parasites per microliter. Mass spectra from purified ring-stage cultures, prepared as described in Example 1, with high and low levels of ring-stage parasitemia are compared in FIG. 5. The results in FIG. 5B show that less than 30 ring-stage parasites deposited and dried inside the well of a metal slide, produce a mass spectrum with a signal-to-noise ratio better than about 25. FIG. 5C shows the same spectrum with 6,000 parasites per well. The reproducible mass spectral "signature" of the heme under a variety of LD TOF conditions allows unambiguous parasite identification even in the presence of contaminant peaks. Optical microscopy examination of the sample spot showed that less than about one-fifth of the surface area of the deposited sample was laser-illuminated using linear laser beam rastering.

These results show that LD-TOF mass spectrometry can be used to quantify levels of parasitemia using known standards for comparisons. The limit of resolution is currently at 10 parasites per microliter blood using the lysis/concentration method described in Example 1.

The literature has reported the time course of *P. yoelli* infection in in vivo mouse models using optical microscopy analysis to calculate levels of parasitemia. Data from Vigario et al. [23] and extrapolations from this data indicate that RBC counts drop off precipitously immediately after infection until about day 20, at which time they rise equally fast to normal levels. The number of parasites per RBC changes in an inverse correlation to this. The number of parasites/RBC increases rapidly from about day 3 after infection until about day 20, after which there is a very sharp decline such that no parasites are detected in RBCs by day 24. This correlates with the animal's recovery from malaria. By contrast, the parasitemia level increases rapidly from day 3 to about day 8, at which time it plateaus until day 24, at which point it immediately drops to zero. The plateau reflects an equilibrium between the increase in parasite replication and the resurgence of RBC production by the recovering host.

The parasite load in a blood sample can be estimated using the following equation: Parasites/Volume=Parasites/RBC×RBCs/Volume. In terms of absolute number of parasites deposited on the sample and unambiguously detected, the methods developed here are sufficiently sensitive and relevant for clinical parasitemia levels of less than 10 parasites per microliter blood using the lysis/concentration method described in Example 1. The use of desorption/ionization of infrared- or visible-wavelength lasers at resonant absorption frequencies for porphyrins is also expected to improve the threshold of detection for a given volume of sample interrogated.

The results show the specific mass/charge signature for free heme. The integrated heme signal was very strong. The signal intensity was roughly consistent with that projected for a sample having high parasitemia level based on data extrapolated from whole blood dilution of *P. falciparum* mixed stage cultures and *P. yoelli* mouse model data.

Some patients with malaria go through a period of anemia when the destruction of RBCs occurs at a faster rate than the body can keep pace with, thus causing the hematocrit to drop. The effect of hematocrit on detection sensitivity and quantitation was evaluated using the direct deposit method with diluted, cultured *P. falciparum*-infected RBCs in whole blood by measuring the number of heme detections of laser scans of the surface of about 1 microliter of prepared sample. For a sample thickness of about 100 microns, the amount of blood scanned is about 0.1 microliters using 20 wells on the Kompact IV instrument slide for the measurement. The number of spatially-contiguous clusters of heme detections was a function of the sample parasite density and the hematocrit, where higher heme counts were seen at lower hematocrits, indicating a higher detection sensitivity for a given sample volume.

Using signal processing to reject background clutter from whole blood can increase the clarity of the heme signal. To accomplish this, an individual laser shot spectrum is run through a matched filter for heme that reduces background clutter to produce a filtered average. This signal processing method is illustrated in FIG. 6 which shows the average LD-TOF spectrum from a direct-deposited sample of cultured RBCs infected with *P. falciparum* and diluted in whole human blood with and without filtering out background noise. It has been discovered that detection of malaria parasites with the mass spectrometric methods described herein is more sensitive and efficient than detection by optical microscopy (which currently requires scanning a stained blood sample by a skilled technician), for a specified blood sample analysis time. LD-TOF measurements are also less prone to sensitivity losses due to sample preparation and handling issues, such as missed detections of parasites due to poor staining when the stain is not fresh or the solution pH is not within the accepted range. Evidence for improved sensitivity and efficiency of the LD-TOF mass spectrometry method and its quantitative aspects is illustrated in FIG. 7A, which shows laser LD-TOF mass spectrometry-based detection of heme in clinical samples from humans infected with either *P. vivax* or *P. falciparum*. The blood samples from patients used in the experiments shown in FIG. 7 were prepared using the method described in Example 1. Due to the small sample size, the data were grouped for each species according to general clinical levels of parasitemia: low=less than 150 parasites per microliter of whole blood; medium=from about 1000 to about 3200 parasites per microliter; and high=from about 25,000 to about 60,000 parasites per microliter. The average number of heme detections tracks the average parasitemia reported by two expert microscopists from optical microscopy measurements obtained for each level for each species. Ten negative cases were reported by the microscopists, and for seven of those cases, LD-TOF mass spectrometry yielded a small, but clearly positive number of heme detections. Subsequent analysis of all 10 cases reported as "negative" for malaria parasites by microscopy indicated that indeed 7 out of the 10 cases was positive for malaria based on both parasite DNA (using PCR analysis), and the presence in the sample of aldolase, a parasite protein. These results were in complete agreement with the LD-TOF mass spectrometry results for the 10 cases (FIG. 7B).

The methods of the present invention can be applied to detect the presence of any parasite or microorganism, including bacteria, that concentrate unbound heme in any animal. Malaria parasites also infect birds and other animals in addition to mammals. In some cases, the parasite or microorganism may be outside the animal's cells, such as parasites that live in the intestinal tract and can be detected in feces. The mass spectrometric methods of the present invention can be used to detect these heme-concentrating extracellular parasites or microorganisms in a biological sample from the animal. The biological sample can be a tissue or fluid sample, or feces. Preparation of the test sample from such biological samples may require various purification steps. Once the test sample is formed on the support, it is analyzed by mass spectrometry as described above. If it is determined that the mass spectrum of the test sample shows the mass/charge signature of unbound heme, it can be concluded that unbound heme-concentrating microorganisms are present in the biological sample.

4. EXAMPLES

4.1 Example 1

Method For Concentrating Unbound Heme In A Sample From A *P. Falciparum* Culture For Subsequent LD-TOF Mass Spectrometry Parasite Detection.

In those experiments in which the blood samples were lysed and washed prior to analysis (the results of which are shown in FIGS. 1-5 and 7), samples were prepared as follows. *P. falciparum* strain 3D7 was maintained in culture as described by Trager and Jensen [26]. Briefly, parasites were cultured at 5% hematocrit, Hct, ($5\times10^5$ human RBC/microliter) in RPMI 1640 growth medium (#31800-022, Gibco-Life Technology, Rockville, Md.), supplemented with 50 micrograms/ml hypoxanthine, 25 millimolar (mM) HEPES buffer (#391338, Calbiochem, San Diego, Calif.), heat-inactivated (56° C., 30 min) O$^+$ normal human sera, and 0.26% $NaHCO_3$. Parasite cultures were kept in an incubator at 37° C. with daily changes of the growth medium. When parasitemia levels reached 3-4%, as determined by Giemsa-stained thin smears and optical microscopy, parasites were sub-cultured by up to 10-fold dilution of the donor culture in fresh medium and fresh uninfected human erythrocytes. A gas mixture of 5% $CO_2$, 5% $O_2$ and 90% $N_2$ was infused into the culture. For culture synchronization, a mixed stage (non-synchronized) culture was collected by centrifugation at $3\times10^3$ g for 10 min. The pellet was then re-suspended in 2 volumes of 5% sorbitol and incubated at 37° C. for 10 minutes.

Late stage parasites are lysed by the sorbitol treatment, in contrast to the ring-stage parasites, which remain intact. Two different agents for initial RBC lysis prior to clean-up—acetic acid (1%) or saponin (0.15%). Higher overall sensitivity of the method was obtained using acetic acid.

Parasites were then washed three times with RPMI 1640 media by centrifugation at $3\times10^3$ g for 10 minutes to remove traces of sorbitol. Parasites were returned back to culture in a fresh medium. CAUTION: Proper procedures ("Biohazard level two") should be followed when handling human blood plasma [15].

Samples for mass spectrometry analysis were prepared according to described procedures. [27] Parasites were collected when the culture reached the desired parasitemia level (typically around 5%, or $2.5\times10^4$ parasites/microliter). Serial dilutions of the parasite suspensions in 5% Hct (hematocrit) and RPMI 1640 were performed. Samples (2 milliliter) were centrifuged at $10^4$ g for 10 minutes. Pellets were washed twice with PBS (phosphate buffered saline). Finally, all samples were resuspended in PBS to the same initial volume. Sample suspensions were kept frozen at minus 20 degrees Celsius before mass spectrometry. All sample preparation procedures involving live *P. falciparum* were performed in a laminar flow hood in a BL2-rated laboratory.

After the clean-up, the sample was frozen. Frozen samples were thawed before analysis, and typically 0.3 microliter from each sample was deposited in a 2×1 mm$^2$ well on the stainless steel sample holder. Samples were allowed to dry in air prior to introduction into the TOF instrument. Freezing and thawing of the samples is not necessary for this method, but is rather a convenient way to store samples for a later test run. The lysis/concentration method described here is the method that is advantageous for low level parasite detection.

4.2 Example 2

Direct Deposit Method For LD-TOF Mass Spectrometry Detection Of Unbound Heme In A Malaria-Infected Blood Sample The presence of malaria-causing parasites can be detected in an animal blood sample using LD-TOF mass spectrometry by depositing a thin layer of blood without lysing the sample. The results illustrated in FIGS. 6A and 6B are from patient samples prepared by the direct deposit method. Typically, the blood sample is diluted about ten-fold to a hematocrit of about 5%, deposited on a metal slide and allowed to dry before inserting the slide (or other support) into a mass spectrometer for analysis of unbound heme sequestered in the parasites. Freezing and thawing of the sample does not affect heme detection and is not required. The hematocrit of a blood sample may vary depending on the stage of the disease. Low levels of parasitemia are best detected with a sample having a hematocrit from about 5% to about 10%. In principle, malaria parasites can be detected at any physiologic or artificially prepared (via dilution) hematocrit. The desired range of hematocrit is that which provides the highest probability of probing the infected RBCs with the laser via scanning the surface of the sample. Higher dilutions yield configurations closer to monolayers and increase this probability, but such configurations generally will require scanning a larger area to find the same number of parasites (increasing the time to detect) as compared to a less dilute sample. On the other hand, too dense a sample can dramatically reduce the surface density of infected RBCs, with a concomitant reduction in sensitivity for a chosen, fixed assay time.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for detecting the presence of malaria parasites in red blood cells from an animal using mass spectrometry, comprising:
    a. obtaining a blood sample from the animal,
    b. preparing, on a support, a test sample from the blood sample,
    c. inserting the support into a mass spectrometer,
    d. obtaining a mass spectrum of the test sample,
    e. determining whether the mass spectrum shows a mass/charge signature of unbound heme, and f. if it is determined that the mass spectrum shows the mass/charge signature of unbound heme, concluding that the animal is infected with malaria parasites.

2. The method of claim 1, said step b of preparing the test sample further comprising performing the steps of:
   1. diluting the blood sample in a buffer solution to form a diluted blood sample;
   2. depositing the diluted blood sample on the support; and
   3. drying the diluted blood sample on the support to form the test sample.

3. The method of claim 1, said step b of preparing the test sample further comprising performing the steps of:
   1. lysing the red blood cells in the blood sample to form a lysate,
   2. washing the lysate;
   3. suspending the washed lysate in a buffered solution to form a buffered lysate;
   4. depositing the buffered lysate on the support; and
   5. drying the buffered lysate on the support to form the test sample.

4. The method of claim 3, said step of lysing the red blood cells further comprising using a lysing agent selected from the group consisting of sorbitol, saponin, and acetic acid.

5. The method as in claim 3, wherein the blood taken from the animal has a hematocrit less than or equal to the normal physiologic value of about 50%.

6. The method of claim 3, wherein the blood taken from the animal has a low level of parasitemia.

7. The method of claim 1, further comprising, if it is determined that the mass spectrum of the test sample shows the mass/charge signature of unbound heme, then performing the step of determining a level of parasitemia of the test sample.

8. The method of claim 7, the step of determining a level of parasitemia of the test sample, further comprising the steps of:
   1. determining an integrated heme signal of the test sample; and
   2. comparing the integrated heme signal of the test sample to one or more predetermined integrated heme signals, wherein each different predetermined integrated heme signal is associated with a different known level of parasitemia.

9. The method of claim 1, wherein the malaria parasite is a *Plasmodium* protozoan selected from the group comprising *P. vivax, P. falciparum, P. ovale* and *P. malariae*.

10. The method of claim 1, wherein the mass spectrometer is a laser desorption mass spectrometer.

11. The method of claim 10, wherein the laser desorption mass spectrometer includes a time of flight mass analyzer.

12. The method of claim 10, wherein the mass spectrometer includes a secondary ion mass spectrometry (SIMS) ion source.

13. The method of claim 10, wherein the mass spectrometer includes a Fourier transform ion cyclotron resonance analyzer.

14. The method of claim 10, wherein the mass spectrometer includes an infrared laser.

15. The method of claim 10, wherein the mass spectrometer includes a visible laser.

16. The method of claim 1, said step e of determining whether the mass spectrum shows a mass/charge signature of unbound heme comprising the step of using a matched filter for heme to reject non-specific background clutter in the mass spectrum.

17. A method for detecting the presence in a biological sample from an animal of microorganisms that concentrate unbound heme, comprising:
   a. obtaining a biological sample from the animal,
   b. preparing, on a support, a test sample from the biolocii-cal sample,
   c. inserting the support into a mass spectrometer,
   d. obtaining a mass spectrum of the test sample,
   e. determining whether the mass spectrum shows a mass/charge signature of unbound heme, and
   f. if it is determined that the mass spectrum shows the mass/charge signature of unbound heme, concluding that the animal is infected with the microorcianisms.

18. The method of claim 17, wherein the microorganisms are parasites that are members of the phylum *Apicomplexa*.

19. The method of claim 17, wherein the microorganisms are parasites members of the family *Shistosomatidae*.

20. The method of claim 1 or claim 17, wherein the animal is a human.

21. The method of claim 17, wherein the microorganisms are bacteria that concentrate unbound heme.

22. The method of claim 17, wherein the biological sample is animal tissue.

23. The method of claim 17, wherein the biological sample is animal fluid.

24. The method of claim 17, wherein the microorganisms are malaria parasites.

* * * * *